(12) United States Patent
Yu et al.

(10) Patent No.: US 6,893,844 B1
(45) Date of Patent: May 17, 2005

(54) DNA ENCODING A NEW HUMAN HEPATOMA DERIVED GROWTH FACTOR AND PRODUCING METHOD THEREOF

(75) Inventors: Long Yu, Handan Road 220, Institute of Genetics, Fudan University, Shanghai (CN), 200433; Honglai Zhang, Shanghai (CN); Qiang Fu, Shanghai (CN); Yong Zhao, Shanghai (CN); Qiang Tu, Shanghai (CN)

(73) Assignee: Long Yu, Shanghai (CN)

( * ) Notice: Subject to any disclaimer, the term of this patent is extended or adjusted under 35 U.S.C. 154(b) by 0 days.

(21) Appl. No.: 09/787,328

(22) PCT Filed: Jun. 9, 1999

(86) PCT No.: PCT/CN99/00139

§ 371 (c)(1),
(2), (4) Date: Mar. 16, 2001

(87) PCT Pub. No.: WO00/17351

PCT Pub. Date: Mar. 30, 2000

(30) Foreign Application Priority Data

Sep. 22, 1998 (CN) .......................................... 98119758 A

(51) Int. Cl.⁷ ......................... C12N 15/18; C12N 15/63; C12N 15/70; C12N 15/79
(52) U.S. Cl. .................. 435/69.4; 435/325; 435/252.3; 435/320.1; 536/23.51
(58) Field of Search ...................... 536/23.51; 435/69.4, 435/325, 252.3, 320.1

(56) References Cited

U.S. PATENT DOCUMENTS 6,468,758 B1 * 10/2002 Benson et al. ............. 435/7.23

FOREIGN PATENT DOCUMENTS

| JP | 05134258 | 12/1994 |
| JP | 6343470 | 12/1994 |
| JP | 08064001 | 9/1997 |
| JP | 9252777 | 9/1997 |

OTHER PUBLICATIONS

Izumoto et al., "Hepatoma–derived growth factor belongs to a gene family in mice showing significant homology in the amino terminus," *Biochem. Biophys. Res. Commun.* 238 (1), 26–32 (1997).

Nakamura et al., "Molecular cloning of complementary DNA for a novel human hepatoma–derived growth factor. Its homology with high mobility group–1 protein," *J. Biol. Chem.* 269 (40), 2514325149 (1994).

Nakamura et al., "Partial purification and characterization of human hepatoma–derived growth factor," *Clin. Chim. Acta.* 183 (3) 273–284 (1989), Abstract only.

Jhappan et al., "TGFα overexpression in transgenic mice induces liver neoplasia and abnormal development of the mammary gland and pancreas," *Cell* vol. 61, 1137–1146 (1990).

Kan et al., "Heparin–binding growth factor type 1 (acidic fibroblast growth factor): A potential biphasic autocrine and paracrine regulator of hepatocyte regeneration," *Proc. Natl. Acad. Sci.* vol. 86, 7432–7436 (1989).

Klagsbrun et al., "Human tumor cells synthesize an endothelial cell growth factor that is structurally related to basic fibroblast growth factor," *Proc. Natl. Acad. Sci.* vol. 83, 2448–2452 (1986).

* cited by examiner

*Primary Examiner*—Robert C. Hayes
(74) *Attorney, Agent, or Firm*—Merchant & Gould P.C.

(57) ABSTRACT

The invention provides a cDNA sequence of a new type II human hepatoma derived growth factor (HDGF2). The protein encoded by such sequence is a homology of type I HDGF. The present invention also relates to peptides encoded by the nucleotide sequences, to uses of these polynucleotide and the polypeptides, and methods for producing the polynucleotides and the polypeptides.

9 Claims, 4 Drawing Sheets

```
human HDGF2 Nt  - ACCGCTCGTCCGCCCGGCTTGAGGCCCGCGGGGAGCGCGCGCAATTCGTC  50
                                                    |||||   |
mouse HDGF Nt   -                                   CGCAAAC-TTG        10 human HDGF2 Nt  - GGCCCGCGGGGGGGCGGCCTCCCGGCATCTTCGCGGCGACCAAGGACTAC  100
                  ||| ||||        . |||||||  |  ||||| | ||   || |  |
mouse HDGF Nt   - GGCTCGCGC------------TTCCCGGCT-CGGCGCGGAGCCCGG-GGCGCC  49 human HDGF2 Nt  - CAGGAAGGGGAGCGGCTGGGATGGCGCG-TCCG---CGGCCCCGCGAGTAC  147
                  |        || | ||    || |||| |||   ||||       |||||
mouse HDGF Nt   - CG-----CGGCCCCGCCA---TGTCGCGATCCAACCGGCAGAAAGAGTAC  91 human HDGF2 Nt  - AAAGCGGGCGACCTGGTCTTCGCCAAGATGAAGGGCTACCCGCACTGGCC  197
                  ||    || |||||||| || ||  |||||||| ||||| ||||||||
mouse HDGF Nt   - AAGTGCGGAGACCTGGTGTTTGCGAAGATGAAAGGATACCCACACTGGCC  141 human HDGF2 Nt  - GGCCCGGATTGATGAACTCCCAGAGGGCGCTGTGAAGCCTCCAGCAAACA  247
                  ||||||||||||||  | || |||| || |||||| |  |||| ||||
mouse HDGF Nt   - GGCCCGGATTGATGAGATGCCTGAGGCTGCAGTGAAGTCAACAGCCAACA  191 human HDGF2 Nt  - AGTATCCTATCTTCTTTTTTGGCACCCATGAAACTGCATTTCTAGGTCCC  297
                  | || |   ||||  ||||||||||  |||||   ||| ||  ||  |||
mouse HDGF Nt   - AATACCAAGTCTTTTTTTTTGGGACCCATGAGACGGCATTCCTGGGCCCC  241 human HDGF2 Nt  - AAAGACCTTTTTCCATATAAGGAGTACAAAGACAAGTTTGGAAAGTCAAA  347
                  |||||||   ||  || |||||  |  |||  |||||||||||  | ||
mouse HDGF Nt   - AAAGACCTCTTCGCTTATGAGGAATCCAAGGAGAAGTTTGGCAAGCCCAA  291 human HDGF2 Nt  - CAAACGGAAAGGATTTAACGAAGGATTGTGGGAAATAGAAAATAACCCAG  397
                  |||  ||||||| ||  |-|||  || ||||||||  ||  ||  |||||
mouse HDGF Nt   - CAAGAGGAAAGGGTTCAGCGAGGGGCTGTGGGAGATCGAGAACAACCCTA  341 human HDGF2 Nt  - GAGTAAAGTTTACTGGCTACCAGGCAATTCAGCAACAGAGCTCTTC---A  444
                   ||| |||    |||||||||||   ||| |||| | ||||| | |   |
mouse HDGF Nt   - CAGTCAAGGCCTCTGGCTACCAGTCCTCCCAGAAAAAGAGTTGTGCGGCA  391 human HDGF2 Nt  - GAAAC----------------TGAGGGAGAAGGTGGAAATAC----   470
                  || |                 ||||||  || ||||    || |
mouse HDGF Nt   - GAGCCCGAGGTGGAGCCCGAAGCCCATGAGGGTGACGGTGATAAGAACGG  441 human HDGF2 Nt  - ---TGCAGATGCAAGCAGTGAGGAAGAAGG--------TGATAGAGTA--  507
                  ||||||  | ||||| || ||||||||     ||||  ||  |
mouse HDGF Nt   - CAGTGCAGAGGGCAGCAGCGACGAAGAAGGGAAACTGGTGATCGATGAAC  491
```

Fig. 1

```
human HDGF2 Nt  - ----------GAAGAAGATGGAAAAGGCAA-----AAGAA-AGA--------AT  537
                           | |||||| |||||||  |     ||||  |||         ||
mouse HDGF  Nt  - CAGCCAAGGAGAAGAACGAAAAGGGCACGCTGAAGAGGAGAGCAGGGGAT  541 human HDGF2 Nt  - G------------------AAA------AAGCAGGCTCAAAAC----GGA  559
                  |                  |||      ||| || |   | ||    |||
mouse HDGF  Nt  - GTGTTGGAGGACTCCCCTAAACGTCCCAAGGAGTCAGGAGACCATGAGGA  591 human HDGF2 Nt  - AAAAGTCAT----ATA----CTT------------------CA------  576
                  | | ||         |||    |||                  ||
mouse HDGF  Nt  - GCAGGACAAGGAGATAGCTGCCTTGGAGGGTGAGAGGCACCTGCCTGTAG  641 human HDGF2 Nt  - --------AAGAA-ATC------CTCTAAAC-AGTC-----CCGGAAATCT  606
                          ||||| | |      |||| | | || |     || | | ||
mouse HDGF  Nt  - AGGTGGAGAAGAACAGCACCCCCTCTGAGCCAGACTCTGGCCAGGGACCT  691 human HDGF2 Nt  - CCAGGAGATGAAGATGACAAAGA---------CTGCAAAG-AAGAGG---A  644
                  || | ||| ||||| ||   |||         |||| ||| ||||||   |
mouse HDGF  Nt  - CCTGCAGAGGAAGAAGAGGGAGAGGAAGAGGCTGCCAAGGAAGAGGCTGA  741 human HDGF2 Nt  - A---------------------------------AA----CAAA  651
                  |                                  ||    |||
mouse HDGF  Nt  - AGCCCCAGGCGTCAGAGATCATGAGAGCCTGTAGCCACCAATGTTTCAAG  791 human HDGF2 Nt  - AGCAGC---------------TCTGAGGG------TGGAGATGCG  675
                  || |||               |||| | |      ||| || |
mouse HDGF  Nt  - AGGAGCCCCTGCCCCGTTCCTGCTGCTGTCTGGGTGCTACTGGGGAAACT  841 human HDGF2 Nt  - GGCAACGACA--CAA------GAA------------------ACACAACT-  699
                  ||| | | |   |||      |||                  || | |||
mouse HDGF  Nt  - GGCCATGGCCTGCAAACTGGGAACCCTTTCCCACCCTATTTACCCTACTC  891 human HDGF2 Nt  - --TCAG---ACT----TGCAGAAAACC-AGT----GAAG--------GGACCT  730
                    |||    |||     | | |||| ||  |    | ||        || |||
mouse HDGF  Nt  - CCTCACTCACTCTCTCCTCTAAGCCCACTCCTGGAGAGTGTCTTGGCCCT  941 human HDGF2 Nt  - AACTACCA-----------TA-ATGAATGCTG----CATATTAAGAGA--AA  764
                  ||  |||             || ||  |   |||      | | | |||| |
mouse HDGF  Nt  - CACCTCCAGCTCCCTTCCTATATACACCCTGTGCCCCAGGATGAGATGAG  991 human HDGF2 Nt  - CCACAAGAAGGT-TATA----TGTTT------GGTT--------GTCTAA  795
                  |   |  | | ||         |||||      ||||         |||||
mouse HDGF  Nt  - GCCTTTGTATCTCTTTACACTTGTTTCCCAGGGTTTCTGCTGGGGTCTAG  1041 human HDGF2 Nt  - TAT------------TCTTG-----------------------GA  805
                  |               |||||                      ||
mouse HDGF  Nt  - GCTGCTGTTTCCACCTCTTGACACCTCTGCCCTGCTGCAGGCATTCTAGA  1091
```

Fig. 1 (cont.)

```
human HDGF2 Nt  - —TTTG————ATA————————————TGAACCAACACATAG—––   827
                   ||||    |||                 ||||  || | | ||
mouse HDGF Nt   - CCTTTGGGGTGGATAGTGGGCAGGAGTGGAGGTGAAAGAATATAAAGGAG  1141 human HDGF2 Nt  - ———————TCCTTGTTGTCATTCAC————AGAACC————CCAG————    854
                        || | || ||| | |          || ||      ||||
mouse HDGF Nt   - TGTGGGTTCATGGATGGCATCGTCTACCTGAGCTCCTGTCTCCAGCCCCC  1191 human HDGF2 Nt  - ————————TTTG————TATG—–TACATT————————————————     868
                          |||     |||  ||||||
mouse HDGF Nt   - ACACTTATTTTCCCATCTGCCTACATTCAAGAAACAGGACACTGTGGGAG  1241 human HDGF2 Nt  - ——————————ATTCAT—ATTCCTCTCTGTTGTGTTTCGGG————      897
                            || |||  ||   ||  ||||||  ||| |||
mouse HDGF Nt   - AGAGGCTACCATCCATCCATAAATCCTTGTTGATTTTTGGGAACACTTAT  1291 human HDGF2 Nt  - ——————————GGGAA-AAGACATTTTAGC————————CTTT—       919
                             |||   |||  ||| |||            ||||
mouse HDGF Nt   - CCCCCTGACCCCAGGGTTCAAGGAATTGTAGTTTAACATCTAGACTTTCG  1341 human HDGF2 Nt  - ——TTTAAAAGTT—————————————————————————————         929
                    |||  |||||
mouse HDGF Nt   - AGTTTCCAAGTTTGGGCCTAGGACCTGGAGGGAGCTAAGAGCTGAAGAAT  1391 human HDGF2 Nt  - ——ACTGATTTAATTTCA————TGT-TATTTGGTT————GCATGAA——   963
                    ||||||||   || |      ||| | ||| | |      ||| ||
mouse HDGF Nt   - CAACTGATTTGCATTGAGGAAATGTCTCTTTAGATCTCAGGGCAGAAATG  1441 human HDGF2 Nt  - —————————————GTTGCCCTTAACCACT————AAGGATTAT———C   989
                               | |||| | | | |||    || | ||      |
mouse HDGF Nt   - ATAACCTGGGGAGACCTGCTGCCTTCATCTACTTCGCAATGCTTGAGGCC  1491 human HDGF2 Nt  - —A————————AGATTTTTG-CGCAGACTTATA————CATGTCT—    1018
                   |         |||| |||  | ||||| || |          ||| | |
mouse HDGF Nt   - AGCCTGTAGTCAGATATTTCACCCAGACATAAAGGAAAAGACCATTTTTT  1541 human HDGF2 Nt  - ——AGGATC              1024  (SEQ ID NO: 3)
                    ||||
mouse HDGF Nt   - TTACGAAATGTTTTTAATAAAA 1563  (SEQ ID NO: 9)
```

Identity: 68.7%

Fig. 1 (cont.)

| | | |
|---|---|---|
| human HDGF2 | – MARP-RPRBYKACDLVPAKMKGYPHWPARIDELPEGAVKPPANKYPIPFF | 49 |
| | ‖·‖ ‖·‖‖ ‖‖‖‖‖‖‖‖‖‖‖‖‖‖‖‖‖‖‖·‖‖ ‖‖‖ ‖‖‖‖·‖‖‖ | |
| mouse HDGF | – MSRSNRQKBYKCGDLVFAKMKGYPHWPARIDEMPBAAVKSTANKYQVFFF | 50 |
| human HDGF2 | – GTHBTAFLGPKDLFPYKEYKDKFGKSNKRKGFNEGLWBIBNNPGVKFTGY | 99 |
| | ‖‖‖‖‖‖‖‖‖‖‖‖‖‖‖‖ ‖ ‖·‖‖‖‖ ‖‖‖‖‖‖ ‖‖‖‖‖‖‖‖‖‖ ‖‖ ·‖‖ | |
| mouse HDGF | – GTHETAFLGPKDLFPYBESKEKFGKPNKRKGFSEGLWBIBNNPTVKASGY | 100 |
| human HDGF2 | – QAIQQQSSS——BTBGEGGN——TADASSEBBGDRVEBDGKGKRKN | 139 |
| | ‖· ‖ ‖· ‖‖ ‖ ·‖· ‖‖·‖‖‖ ·· ‖ ‖‖‖ | |
| mouse HDGF | – QSSQKKSCAABPBVBPBAHEGDGDKKGSABGSSDBBG-KLVIDEPAKBKN | 149 |
| human HDGF2 | – EKAGSKRKKSYTSKKSSKQSRKSPGDEDD———————— | 168 |
| | ‖‖ ‖‖· ‖‖·‖ ‖·· | |
| mouse HDGF | – BKGTLKRRAGDVLBDSPKRPKESGDHBBEDKBIAALBGERHLPVBVBKNS | 199 |
| human HDGF2 | – ——————————KDCKBBENKSSSBGGDAGNDTRNTTSDLQKTSBGT | 203 (SEQ ID NO: 4) |
| | · ‖‖ ‖ ·‖ ‖ | |
| mouse HDGF | – TPSEPDSGQGPPAEBBEGEEBAAKEEAEAPGVRDH——————ESL | 237 (SEQ ID NO: 10) |

Identity: 53.7%
Similarity: 9.4%

Fig. 2

SEQUENCE LISTING

<160> NUMBER OF SEQ ID NOS: 10

<210> SEQ ID NO 1
<211> LENGTH: 23
<212> TYPE: DNA
<213> ORGANISM: Artificial Sequence
<220> FEATURE:
<223> OTHER INFORMATION: Synthetic primer for polymerase chain reaction
      (PCR)

<400> SEQUENCE: 1
accgctcgtc cgcccggctt gag                                          23

<210> SEQ ID NO 2
<211> LENGTH: 26
<212> TYPE: DNA
<213> ORGANISM: Artificial Sequence
<220> FEATURE:
<223> OTHER INFORMATION: Synthetic primer for polymerase chain reaction
      (PCR)

<400> SEQUENCE: 2
gatcctagac atgtataagt ctgcgc                                       26

<210> SEQ ID NO 3
<211> LENGTH: 1024
<212> TYPE: DNA
<213> ORGANISM: Homo sapiens

<400> SEQUENCE: 3
accgctcgtc cgcccggctt gaggcccgcg gggagcgcgc gcaattcgtc ggcccgcggg      60
ggggcggcct cccggcatct tcgcggcgac caaggactac caggaagggg agcggctggg    120

```
atggcgcgtc cgcggccccg cgagtacaaa gcgggcgacc tggtcttcgc caagatgaag      180
ggctacccgc actggccggc ccggattgat gaactcccag agggcgctgt gaagcctcca      240
gcaaacaagt atcctatctt cttttttggc acccatgaaa ctgcatttct aggtcccaaa      300 gaccttttc catataagga gtacaaagac aagtttggaa agtcaaacaa acggaaagga       360
tttaacgaag gattgtggga aatagaaaat aacccaggag taaagtttac tggctaccag      420
gcaattcagc aacagagctc ttcagaaact gagggagaag gtggaaatac tgcagatgca      480
agcagtgagg aagaaggtga tagagtagaa gaagatggaa aaggcaaaag aaagaatgaa      540
aaagcaggct caaaacggaa aaagtcatat acttcaaaga atcctctaa acagtcccgg       600 aaatctccag gagatgaaga tgacaaagac tgcaaagaag aggaaaacaa aagcagctct      660
gagggtggag atgcgggcaa cgacacaaga aacacaactt cagacttgca gaaaaccagt      720
gaagggacct aactaccata atgaatgctg catattaaga gaaaccacaa gaaggttata      780
tgtttggttg tctaatattc ttggatttga tatgaaccaa cacatagtcc ttgttgtcat      840
tgacagaacc ccagtttgta tgtacattat tcatattcct ctctgttgtg tttcgggggg      900
aaaagacatt ttagccttt ttaaaagtta ctgatttaat ttcatgttat ttggttgcat       960
gaagttgccc ttaaccacta aggattatca agattttgc gcagacttat acatgtctag       1020
gatc                                                                   1024
```

<210> SEQ ID NO 4
<211> LENGTH: 203
<212> TYPE: PRT
<213> ORGANISM: Homo sapiens

<400> SEQUENCE: 4

Met Ala Arg Pro Arg Pro Arg Glu Tyr Lys Ala Gly Asp Leu Val Phe
1               5                   10                  15

Ala Lys Met Lys Gly Tyr Pro His Trp Pro Ala Arg Ile Asp Glu Leu
            20                  25                  30

Pro Glu Gly Ala Val Lys Pro Pro Ala Asn Lys Tyr Pro Ile Phe Phe
        35                  40                  45

Phe Gly Thr His Glu Thr Ala Phe Leu Gly Pro Lys Asp Leu Phe Pro
    50                  55                  60

Tyr Lys Glu Tyr Lys Asp Lys Phe Gly Lys Ser Asn Lys Arg Lys Gly
65                  70                  75                  80

Phe Asn Glu Gly Leu Trp Glu Ile Glu Asn Asn Pro Gly Val Lys Phe
                85                  90                  95

Thr Gly Tyr Gln Ala Ile Gln Gln Ser Ser Glu Thr Glu Gly
            100                 105                 110

Glu Gly Gly Asn Thr Ala Asp Ala Ser Ser Glu Glu Gly Asp Arg
        115                 120                 125

Val Glu Glu Asp Gly Lys Gly Lys Arg Lys Asn Glu Lys Ala Gly Ser
    130                 135                 140

Lys Arg Lys Lys Ser Tyr Thr Ser Lys Lys Ser Ser Lys Gln Ser Arg
145                 150                 155                 160

Lys Ser Pro Gly Asp Glu Asp Lys Asp Cys Lys Glu Glu Asn
                165                 170                 175

Lys Ser Ser Ser Glu Gly Gly Asp Ala Gly Asn Asp Thr Arg Asn Thr
            180                 185                 190

Thr Ser Asp Leu Gln Lys Thr Ser Glu Gly Thr
        195                 200

```
<210> SEQ ID NO 5
<211> LENGTH: 29
<212> TYPE: DNA
<213> ORGANISM: Artificial Sequence
<220> FEATURE:
<223> OTHER INFORMATION: Synthetic primer for polymerase chain reaction
      (PCR)

<400> SEQUENCE: 5
ccacggatcc atggcgcgtc cgcggcccc                              29

<210> SEQ ID NO 6
<211> LENGTH: 29
<212> TYPE: DNA
<213> ORGANISM: Artificial Sequence
<220> FEATURE:
<223> OTHER INFORMATION: Synthetic primer for polymerase chain reaction
      (PCR)

<400> SEQUENCE: 6
atccgtcgac ttaggtccct tcactggtt                              29

<210> SEQ ID NO 7
<211> LENGTH: 29
<212> TYPE: DNA
<213> ORGANISM: Artificial Sequence
<220> FEATURE:
<223> OTHER INFORMATION: Synthetic primer for polymerase chain reaction
      (PCR)

<400> SEQUENCE: 7
ccctaagctt atggcgcgtc cgcggcccc                              29

<210> SEQ ID NO 8
<211> LENGTH: 29
<212> TYPE: DNA
<213> ORGANISM: Artificial Sequence
<220> FEATURE:
<223> OTHER INFORMATION: Synthetic primer for polymerase chain reaction
      (PCR)

<400> SEQUENCE: 8
tttcggatcc ttaggtccct tcactggtt                              29

<210> SEQ ID NO 9
<211> LENGTH: 1563
<212> TYPE: DNA
<213> ORGANISM: Mus musculus

<400> SEQUENCE: 9
cgcaaacttg ggctcgcgct tcccggctcg gcgcggagcc cggggcgccc gcggccccgc    60
catgtcgcga tccaaccggc agaaagagta caagtgcgga gacctggtgt ttgcgaagat   120
gaaaggatac ccacactggc cggcccggat tgatgagatg cctgaggctg cagtgaagtc   180
aacagccaac aaataccaag tcttttttttt tgggacccat gagacggcat tcctgggccc   240
caaagacctc ttcccttatg aggaatccaa ggagaagttt ggcaagccca acaagaggaa   300
agggttcagc gagggggctgt gggagatcga gaacaaccct acagtcaagg cctctggcta   360
ccagtcctcc cagaaaaaga gttgtgcggc agagcccgag gtggagcccg aagcccatga   420
gggtgacggt gataagaagg gcagtgcaga gggcagcagc gacgaagaag ggaaactggt   480
gatcgatgaa ccagccaagg agaagaacga aagggcacg ctgaagagga gagcagggga   540
tgtgttggag gactccccta aacgtcccaa ggagtcagga gaccatgagg aggaggacaa   600
```

-continued

```
ggagatagct gccttggagg gtgagaggca cctgcctgta gaggtggaga agaacagcac   660
cccctctgag ccagactctg gccagggacc tcctgcagag gaagaagagg gagaggaaga   720
ggctgccaag gaagaggctg aagccccagg cgtcagagat catgagagcc tgtagccacc   780
aatgtttcaa gaggagcccc tgccccgttc ctgctgctgt ctgggtgcta ctggggaaac   840
tggccatggc ctgcaaactg gaaccctttt ccacccctat ttaccctact ccctcactca   900
ctctctcctc taagcccact cctggagagt gtcttggccc tcacctccag ctcccttcct   960
atatacaccc tgtgcccag gatgagatga ggcctttgta tctctttaca cttgttccc   1020 agggtttctg ctggggtcta ggctgctgtt tccacctctt gacacctctg ccctgctgca   1080
ggcattctag acctttgggg tggatagtgg gcaggagtgg aggtgaaaga atataaagga   1140
gtgtgggttc atggatggca tcgtctacct gagctcctgt ctccagcccc cacacttatt   1200
ttcccatctg cctacattca agaaacagga cactgtggga gagaggctac catccatcca   1260
taaatccttg ttgattttg ggaacactta tccccctgac cccagggttc aaggaattgt   1320
agtttaacat ctagactttg gagtttccaa gtttgggcct aggacctgga gggagctaag   1380
agctgaagaa tcaactgatt tgcattgagg aaatgtctct ttagatctca gggcagaaat   1440
gataacctgg ggagacctgc tgccttcatc tacttcccaa tgcttgaggc agcctgtag    1500 tcagatattt cacccagaca taaggaaaa gaccattttt tttaggaaat gtttttaata   1560
aaa                                                                1563
```

<210> SEQ ID NO 10
<211> LENGTH: 237
<212> TYPE: PRT
<213> ORGANISM: Mus musculus

<400> SEQUENCE: 10

```
Met Ser Arg Ser Asn Arg Gln Lys Glu Tyr Lys Cys Gly Asp Leu Val
1               5                   10                  15

Phe Ala Lys Met Lys Gly Tyr Pro His Trp Pro Ala Arg Ile Asp Glu
            20                  25                  30

Met Pro Glu Ala Ala Val Lys Ser Thr Ala Asn Lys Tyr Gln Val Phe
        35                  40                  45

Phe Phe Gly Thr His Glu Thr Ala Phe Leu Gly Pro Lys Asp Leu Phe
    50                  55                  60

Pro Tyr Glu Glu Ser Lys Glu Lys Phe Gly Lys Pro Asn Lys Arg Lys
65                  70                  75                  80

Gly Phe Ser Glu Gly Leu Trp Glu Ile Glu Asn Asn Pro Thr Val Lys
                85                  90                  95

Ala Ser Gly Tyr Gln Ser Ser Gln Lys Lys Ser Cys Ala Ala Glu Pro
            100                 105                 110

Glu Val Glu Pro Glu Ala His Glu Gly Asp Gly Asp Lys Lys Gly Ser
        115                 120                 125

Ala Glu Gly Ser Ser Asp Glu Glu Gly Lys Leu Val Ile Asp Glu Pro
    130                 135                 140

Ala Lys Glu Lys Asn Glu Lys Gly Thr Leu Lys Arg Arg Ala Gly Asp
145                 150                 155                 160

Val Leu Glu Asp Ser Pro Lys Arg Pro Lys Glu Ser Gly Asp His Glu
                165                 170                 175

Glu Glu Asp Lys Glu Ile Ala Ala Leu Glu Gly Glu Arg His Leu Pro
            180                 185                 190
```

-continued

```
Val Glu Val Glu Lys Asn Ser Thr Pro Ser Glu Pro Asp Ser Gly Gln
        195                 200                 205

Gly Pro Pro Ala Glu Glu Glu Gly Glu Glu Glu Ala Ala Lys Glu
        210             215             220

Glu Ala Glu Ala Pro Gly Val Arg Asp His Glu Ser Leu
225             230             235
```

DNA ENCODING A NEW HUMAN HEPATOMA DERIVED GROWTH FACTOR AND PRODUCING METHOD THEREOF

This application is a National Stage application under U.S.C 371 of International Application No. PCT/CN99/00139, filed Jun. 9, 1999.

FIELD OF INVENTION

This invention relates to the field of genetic engineering, and, in particular, relates to the nucleotide sequence of a novel human gene. More particularly, this invention relates to the cDNA sequence of a novel type II human Hepatoma-derived Growth Factor (HDGF2), which is a homologue of type I HDGF. The invention also relates to the polypeptides encoded by the nucleotide sequence, the uses of these polynucleotides and polypeptides, and the methods for producing them.

PRIOR ART

It is revealed that the regulation of cell growth is mediated by a series of cascade reactions triggered by the interaction between a variety of cytokines and their specific receptors on membrane surfaces. In tumor cells, some steps of cascade reactions appear to be out of control, which results in continuous cellular proliferation. In hepatoma cells, several autocrine and paracrine cell factors were found (Proc. Natl. Acad. Sci. 83:2448–2452, 1986; Proc. Natl. Acad. Sci. 86:7432–7436, 1989; Cell 61: 1137–1146, 1990). Hepatoma-derived Growth Factor (HDGF) was a cytokine identified from human hepatoma derived cell line HuH-7 cultured in serum-free medium. HDGF had the heparin-binding activity and stimulated the DNA synthesis in Swiss 3T3 cell (J. Biol. chem. 269 (40): 25143–25149, 1994).

In 1989, HDGF was first partially purified from HuH-7 cells and characterized by Nakamura et. al. (Clin. Chim. Acta. 183:273–284, 1989). This research group cloned the full length HDGF cDNA sequence in 1994 (J. Biol. Chem. 269(40): 25143–25149, 1994). In 1997, this group found the mouse homologue of human HDGF as well as other two members of the gene family, HRP-1 and HRP-2. They all had a highly conserved N-terminal of 98 amino acids. (Biochem. Biophys. Res. Commun. 238: 26–32, 1997).

Prior to this invention, none has disclosed human HDGF2 of the present application concerns, which is another member of the human HDGF family.

SUMMARY OF INVENTION

One purpose of the invention is to provide a new polynucleotide which encodes a homologue of HDGF. In the invention, the gene of said homologue of HDGF is named HDGF2.

Another purpose of the invention is to provide a novel protein, which is named HDGF2.

Still another purpose of the invention is to provide a new method for preparing said new HDGF2 protein by recombinant techniques.

The invention also relates to the uses of said HDGF2 protein and its coding sequence.

In one aspect, the invention provides an isolated DNA molecule, which comprises a nucleotide sequence encoding a polypeptide having human HDGF2 protein activity, wherein said nucleotide sequence shares at least 70% homology to the nucleotide sequence of nucleotides 121–732 in SEQ ID NO: 3, or said nucleotide sequence can hybridize to the nucleotide sequence of nucleotides 121–732 in SEQ ID NO: 3 under moderate stringency. Preferably, said nucleotide sequence encodes a polypeptide comprising the amino acid sequence of SEQ ID NO: 4. More preferably, the sequence comprises the nucleotide sequence of nucleotides 121–732 in SE ID NO: 3.

Further, the invention provides an isolated HDGF2 polypeptide, which comprises a polypeptide having the amino acid sequence of SEQ ID NO: 4, its active fragments, and its active derivatives. Preferably, the polypeptide is a polypeptide having the amino acid sequence of SEQ ID NO: 4.

The invention also provides a vector comprising said isolated DNA.

The invention further provides a host cell transformed with said vector.

In another aspect, the invention provides a method for producing a polypeptide with the activity of HDGF2 protein, which comprises:

(a) forming a HDGF2 protein expression vector comprising the nucleotide sequence encoding the polypeptide having the activity of HDGF2 protein, wherein said nucleotide sequence is operably linked with an expression regulatory sequences, and said nucleotide sequence shares at least 70% homology to the nucleotide sequence of positions 121–732 in SEQ ID NO: 3;

(b) introducing the vector of step (a) into a host cell, thereby forming a recombinant cell of HDGF2 protein;

(c) culturing the recombinant cell of step (b) under the conditions suitable/for the expression of HDGF2 polypeptides;

(d) isolating the polypeptides having the activity of HDGF2 protein.

In one embodiment of the present invention, the isolated polynucleotide has a full length of 1024 nucleotides, whose detailed sequence is shown in SEQ ID NO: 3. The open reading frame (ORF) is located at nucleotides 121–732.

In the present invention, the term "isolated" or "purified" or "substantially pure" DNA refers to a DNA or fragment which has been isolated from the sequences which frank it in a naturally occurring state. The term also applies to DNA or DNA fragment which has been isolated from other components naturally accompanying the nucleic acid and from proteins naturally accompanying it in the cell.

In the present invention, the term "HDGF2 protein encoding sequence" or "HDGF2 polypeptide encoding sequence" refers to a nucleotide sequence encoding a polypeptide having the activity of HDGF2 protein, such as the nucleotide sequence of positions 121–732 in SEQ ID NO: 3 or its degenerate sequence. The degenerate sequences means the sequences formed by replacing one or more codons in the ORF of 121–732 in SEQ ID NO: 3 with degenerate codes which encode the same amino acid. Because of the degeneracy of codon, the sequence having a homology as low as about 70% to the sequence of nucleotides 121–732 in SEQ ID NO: 3 can also encode the sequence shown in SEQ ID NO: 4. The term also refers to the nucleotide sequences that hybridize to the nucleotide sequence of nucleotides 121–732 in SEQ ID NO: 3 under moderate stringency or preferably under high stringency. In addition, the term also refers to the sequences having a homology of at least 70%, preferably 80%, more preferably 90% to the nucleotide sequence of nucleotides 121–732 in SEQ ID NO: 3.

The term also refers to variants of the sequence in SEQ ID NO: 3, which are capable of encoding a protein having the same function as human HDGF2 protein. These variants includes, but are not limited to, deletions, insertions and/or substitutions of several nucleotides (typically 1–90, preferably 1–60, more preferably 1–20, and most preferably 1–10) and additions of several nucleotides (typically less than 60, preferably 30, more preferably 10, most preferably 5) at 5' end and/or 3' end.

In the present invention, "substantially pure" proteins or polypeptides refers to those which occupy at least 20%, preferably at least 50%, more preferably at least 80%, most preferably at least 90% of the total sample material (by wet weight or dry weight). Purity can be measured by any appropriate method, e.g., in the case of polypeptides by column chromatography, PAGE or HPLC analysis. A substantially purified polypeptides is essentially free of naturally associated components.

In the present invention, the term "HDGF2 polypeptide" or "HDGF2 protein" refers to a polypeptide having the activity of HDGF2 protein comprising the amino acid sequence of SEQ ID NO: 4. The term also comprises the variants of said amino acid sequence which have the same function of human HDGF2. These variants include, but are not limited to, deletions, insertions and/or substitutions of several amino acids (typically 1–50, preferably 1–30, more preferably 1–20, most preferably 1–10), and addition of one or more amino acids (typically less than 20, preferably less than 10, more preferably less than 5) at C-terminal and/or N-terminal. For example, the protein functions are usually unchanged when an amino residue is substituted by a similar or analogous one. Further, the addition of one or several amino acids at C-terminal and/or N-terminal will not change the function of protein. The term also includes the active fragments and derivatives of HDGF2 protein.

The variants of polypeptide include homologous sequences, allelic variants, natural mutants, induced mutants, proteins encoded by DNA which hybridizes to HDGF2 DNA under high or low stringency conditions as well as the polypeptides or proteins retrieved by antisera raised against HDGF2 polypeptide. The present invention also provides other polypeptides, e.g., fusion proteins, which include the HDGF2 polypeptide or fragments thereof. In addition to substantially full-length polypeptide, the soluble fragments of HDGF2 polypeptide are also included. Generally, these fragments comprise at least 10, typically at least 30, preferably at least 50, more preferably at least 80, most preferably at least 100 consecutive amino acids of HDGF2 polypeptide.

The present invention also provides the analogues of HDGF2 protein or polypeptide. Analogues can differ from naturally occurring HDGF2 polypeptide by amino acid sequence differences or by modifications which do not affect the sequence, or by both. These polypeptides include genetic variants, both natural and induced. Induced variants can be made by various techniques, e.g., by random mutagenesis using irradiation or exposure to mutagens, or by site-directed mutagenesis or other known molecular biologic techniques. Also included are analogues which include residues other than those naturally occurring L-amino acids (e.g., D-amino acids) or non-naturally occurring or synthetic amino acids (e.g., beta- or gamma-amino acids). It is understood that the polypeptides of the invention are not limited to the representative polypeptides listed hereinabove.

Modifications (which do not normally alter primary sequence) include in vivo, or in vitro chemical derivation of polypeptides, e.g., acelylation, or carboxylation. Also included are modifications of glycosylation, e.g., those made by modifying the glycosylation patterns of a polypeptide during its synthesis and processing or in the further processing steps, e.g., by exposing the polypeptide to enzymes which affect glycosylation (e.g., mammalian glycosylating or deglycosylating enzymes). Also included are sequences which have phosphorylated amino acid residues, e.g., phosphotyrosine, phosphoserine, phosphothronine, as well as sequences which have been modified to improve their resistance to proteolytic degradation or to optimize solubility properties.

The invention also includes antisense sequence of the sequence encoding HDGF2 polypeptide. Said antisense sequence can be used to inhibit expression of HDGF2 in cells.

The invention also includes probes, typically having 8–100, preferably 15–50 consecutive nucleotides. These probes can be used to detect the presence of nucleic acid molecules coding for HDGF2 in samples.

The present invention also includes methods for detecting HDGF2 nucleotide sequences, which comprises hybridizing said probes to samples, and detecting the binding of the probes. Preferably, the samples are products of PCR amplification. The primers in PCR amplification correspond to coding sequence of HDGF2 polypeptide and are located at both ends or in the middle of the coding sequence. In general, the length of the primers is 20 to 50 nucleotides.

A variety of vectors known in the art, such as those commercially available, are useful in the invention.

In the invention, the term "host cells" includes prokaryotic and eukaryotic cells. The common prokaryotic host cells include *Escherichi coli, Bacillus subtilis*, and so on. The common eukaryotic host cells include yeast cells, insect cells, and mammalian cells. Preferably, the host cells are eukaryotic cells, e.g., CHO cells, COS cells, and the like.

In another aspect, the invention also includes antibodies, preferably monoclonal antibodies, which are specific for polypeptides encoded by HDGF2 DNA or fragments thereof. By "specificity", it is meant an antibody which binds to the HDGF2 gene products or a fragments thereof. Preferably, the antibody binds to the HDGF2 gene products or a fragments thereof and does not substantially recognize nor bind to other antigenically unrelated molecules. Antibodies which bind to HDGF2 and block HDGF2 protein and those which do not affect the HDGF2 function are included in the invention. The invention also includes antibodies which bind to the HDGF2 gene product in its unmodified as well as modified form.

The present invention includes not only intact monoclonal or polyclonal antibodies, but also immunologically-active antibody fragments, e.g., a Fab' or (Fab)$_2$ fragment, an antibody light chain, an antibody heavy chain, a genetically engineered single chain Fv molecule (Lander, et al., U.S. Pat. No. 4,946,778), or a chimeric antibody, e.g., an antibody which contains the binding specificity of a murine antibody, but the remaining portion of which is of human origin.

The antibodies in the present invention can be prepared by various techniques known to those skilled in the art. For example, purified HDGF2 gene products, or its antigenic fragments can be administrated to animals to induce the production of polyclonal antibodies. Similarly, cells expressing HDGF2 or its antigenic fragments can be used to immunize animals to produce antibodies. Antibodies of the invention can be monoclonal antibodies which can be prepared by using hybridoma technique (See Kohler, et al., Nature, 256; 495, 1975; Kohler, et al., Eur. J. Immunol. 6: 511, 1976; Kohler, et al., Eur. J. Immunol. 6: 292, 1976; Hammerling, et al., In Monoclonal Antibodies and T Cell Hybridomas, Elsevier, N.Y., 1981).

Antibodies of the invention comprise those which block HDGF2 function and those which do not affect HDGF2 function. Antibodies in the invention can be produced by routine immunology techniques and using fragments or functional regions of HDGF2 gene product. These fragments and functional regions can be prepared by recombinant methods or synthesized by a polypeptide synthesizer. Antibodies binding to unmodified HDGF2 gene product can be produced by immunizing animals with gene products produced by prokaryotic cells (e.g., *E. coli*); antibodies binding to post-translationally modified forms thereof can be acquired by immunizing animals with gene products produced by eukaryotic cells (e.g., yeast or insect cells).

The full length human HDGF2 nucleotide sequence or its fragment of the invention can be prepared by PCR amplification, recombinant method and synthetic method. For PCR amplification, one can obtain said sequences by designing primers based on the nucleotide sequence disclosed in the invention, especially the sequence of ORF, and using cDNA library commercially available or prepared by routine techniques known in the art as a template. When the sequence is long, it is usually necessary to perform two or more PCR amplifications and link the amplified fragments together in the correct order.

Once the sequence is obtained, a great amount of the sequences can be produced by recombinant methods. Usually, said sequence is cloned in a vector which is then transformed into a host cell. Then the sequence is isolated from the amplified host cells using conventional techniques.

Further, the sequence can be produced by synthesis. Typically, several small fragments are synthesized and linked together to obtain a long sequence. At present, it is completely feasible to chemically synthesize the DNA sequence encoding the protein of the invention, or the fragments or derivatives thereof. In addition, the mutation can be introduced into the sequence of the protein by chemical synthesis.

In addition to recombinant techniques, the protein fragments of the invention may also be prepared by direct chemical synthesis using solid phase synthesis techniques (Stewart et al., (1969) Solid-Phase Peptide Synthesis, WH Freeman Co., San Francisco; Merrifield J. (1963), J. Am. Chem. Assoc. 85: 2149–2154). In vitro protein synthesis can be performed manually or automatically, e.g., using a Model 431 Peptide Synthesizer (Applied Biosystems, Foster City, Calif.). The fragments of protein of the invention can be synthesized separately and linked together using chemical methods so as to produce full-length molecule.

The sequences encoding the protein of the present invention are also valuable for gene mapping. For example, the accurate chromosome mapping can be performed by hybridizing cDNA clones to a chromosome in metaphase. This technique can use cDNA as short as about 500 bp, or as long as about 2000 bp, or more. For details, see Verma et al., Human Chromosomes: A Manual of Basic Techniques, Pergamon Press, New York (1988).

Once a sequence has been mapped to a precise chromosomal location, the physical position of the sequence on the chromosome can be correlated with genetic map data. Such data are found in, e.g., Mendelian Inheritance in Man (available on-line through Johns Hopkins University Welch Medical Library). The relationships between genes and diseases that have been mapped to the same chromosomal region are then identified through linkage analysis.

Then, the differences in the cDNA or genomic sequence between affected and unaffected individuals can also be determined. If a mutation is observed in some or all of the affected individuals but not in any normal individual, then the mutation is likely to be the causative agent of the disease.

The substances which act with the HDGF2, e.g., receptors, inhibitors and antagonists, can be screened out by various conventional techniques, using the protein of the invention.

The protein, antibody, inhibitor, antagonist or receptor of the invention provide different effects when administrated in therapy. Usually, these substances are formulated with a non-toxic, inert and pharmaceutically acceptable aqueous carrier. The pH typically ranges from 5 to 8, preferably from about 6 to 8, although pH may alter according to the property of the formulated substances and the diseases to be treated. The formulated pharmaceutical composition is administrated in conventional routine including, but not limited to, intramuscular, intraperitoneal, subcutaneous, intracutaneous, or topical administration.

As an example, the human HDGF2 protein of the invention may be administrated together with the suitable and pharmaceutically acceptable carrier. The examples of carriers include, but are not limited to, saline, buffer solution, glucose, water, glycerin, ethanol, or the combination thereof. The pharmaceutical formulation should be suitable for the delivery method. The human HDGF2 protein of the invention may be in the form of injections which are made by conventional methods, using physiological saline or other aqueous solution containing glucose or auxiliary substances. The pharmaceutical compositions in the form of tablet or capsule may be prepared by routine methods. The pharmaceutical compositions, e.g., injections, solutions, tablets, and capsules, should be manufactured under sterile conditions. The active ingredient is administrated in therapeutically effective amount, e.g., from about 1 ug to 5 mg per kg body weight per day. Moreover, the polypeptide of the invention can be administrated together with other therapeutic agent.

When the human HDGF2 polypeptides of the invention are used as a pharmaceutical, the therapeutically effective amount of the polypeptides are administrated to mammals. Typically, the therapeutically effective amount is at least about 10 ug/kg body weight and less than about 8 mg/kg body weight in most cases, and preferably about 10 ug–1 mg/kg body weight. Of course, the precise amount will depend upon various factors, such as delivery methods, the subject health, and the like, and is within the judgment of the skilled clinician.

DESCRIPTION OF DRAWINGS

FIG. 1 shows an alignment comparison of nucleotide sequences of HDGF2 (SEQ ID NO: 3) of the invention and mouse HDGF2 (SEQ ID NO: 9). The identical nucleotides are indicated by "|".

FIG. 2 shows an alignment comparison of amino acid sequences of HDGF2 (SEQ ID NO: 4) of the invention and mouse HDGF2 (SEQ ID NO: 10). The identical and similar amino acids are indicated by "|" and ".", respectively.

In one embodiment, the cDNA sequence of HDGF2 was obtained as follows: human testis λgt 11 cDNA library (Clonetech) was used as a template and PCR was carried out with the synthetic forward primer A1: 5'-ACCGCTCGTC CGCCCGGTT GAG-3' (SEQ ID NO: 1) and reverse primer B: 5'-GATCCTAGAC ATGTATAAGT CTGCGC-3' (SEQ ID NO: 2). Target fragments of 1024 bp were obtained. The sequencing of the PCR product gave the full length cDNA sequence shown in SEQ ID NO: 3.

Hepatoma-derived Growth Factor (HDGF) is a hepatin-binding protein isolated from human hepatoma-derived cell line HuH-7. HDGF has the activity of stimulating cell growth and promoting the growth of fibroblast and some heptoma cells (J. Biol. Chem. 269(40): 25143–25149, 1994). It is expressed in human heart, brain, lung, liver, etc., and several tumor-derived cell lines (J. Biol. Chem. 269(40): 25143–25149, 1994). The expression patterns of the HDGF gene family members are different. However, they are all enriched in testis and the 5'-untranslated region contains GC-rich nucleotide sequences (GC content>70%) (Biochem. Biophys. Res. Comun. 238: 26–32, 1997), suggesting their potential important roles in male germ-cell development. They may also relate to DNA methylation, chromatin conformation, and translational regulation (J. Cell. Biol. 115: 887–903, 1990; Cell 62: 503–514, 1990). Although HDGF protein is located mainly in cytoplasm (J. Biol. Chem. 269(40): 25143–25149, 1994), the amino acid sequences of family members all contain a putative Nuclear Localization Signal (NLS), and none have any signal peptide sequence, which suggests they may play a role in nucleus. Furthermore, the acidic amino acid sequence in the C-terminus of HDGF shares a high homology to that of HMG-1/-2 of HMG family (This sequence is known to be a histone-binding region in HMG-1/-2) (Biochemistry 29: 4419–4423, 1990). It is likely that HDGF functions as a transcriptional factor to stimulate cell growth after internalization (Biochem. Biophys. Res. Comun. 238: 26–32, 1997). The mitogenic activity of HDGF implies the great application value of HDGF in treating pernicious oxyhepatitis and liver injury (Clin. Chim. Acta. 183L 273–284, 1989). Researches indicate that many fibroblast growth factors can be widely applied to the vascularization defects, i.e., ischemia and atherosclerosis, and to neuron development (Blood 91(10): 3527–3561, 1998; Ann. N.Y. Acad. Sci. 545: 240–252, 1998).

The invention is further illustrated by the following examples. It is appreciated that these examples are only intended to illustrate the invention, but not to limit the scope of the invention. For the experimental methods in the following examples, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

EXAMPLE 1

The Cloning and Sequencing of HDGF2 cDNA Sequence

1. Amplification with Primers

The template was human testis λ gt 11 cDNA library (commercially available from Clontech). PCR was carried out with the forward primer A1: 5'-ACCGCTCGTC CGC-CCGGCTT GAG-3' (SEQ ID NO: 1) and reverse primer A2: 5'-GATCCTAGAC ATGTATAAGT CTGCGC-3' (SEQ ID NO: 2). The PCR condition was 4 mins at 93° C.; followed by 35 cycles with 1 min at 93° C., 1 min at 68.5° C., and 1 min at 72° C.; and, finally 5 mins at 72° C. The PCR fragments were detected by electrophoresis. The target fragment was 1024 bp.

2. Sequencing PCR Products

The above obtained PCR products were linked with pGEM-T™ vector (Promega) and transformed into *E. coli* JM103. The plasmids were extracted using QIAprep Plasmid Kit (QIAGEN). The oriented serial deletion of the inserted fragments was carried out with Double-Stranded Nested Deletion Kit (Pharmacia), and the deletants were quickly identified by PCR and arranged in order. The deletants successively cutoff were sequenced with SequiTherm EXCEL™ DNA Sequencing Kit (Epicentre Technologies). A full length cDNA sequence of 1024 bp was obtained by overlapping the sequences with computer software. The detailed sequence is shown in SEQ ID NO: 3 with an open reading frame (ORF) located at nucleotides 121–732.

According to the resultant full-length cDNA sequence, the amino acid sequence of HDGF2 was deduced, having 203 amino acid residues totally. See SEQ ID NO: 4 for its amino acid sequence in details.

EXAMPLE 2

Homologous Comparison

The full length cDNA sequence of human HDGF2 and the encoded protein were used for homologous searching Non-redundant GenBank+EMBL+DDBJ+PDB and on-redundant GenBank CDS translations+PDB+SwissProt+Spupdate+PIR databases by BLAST algorithm. The result showed that they shared high homology to mouse HDGF2 (dbj|D63707|MUSHDGF) gene and its encoded protein. Using PCGENE software, it was found that they shared 68.7% identity at the nucleic acid level and 53.7% identity and 9.4% similarity at the protein level (FIG. 1 and FIG. 2). In particular, the conserved 98-amino acid N-terminal showed 90% homology to mouse HDGF. In addition, human HDGF2 was homologous to another mouse HDGF gene (dbj|D63850|MUSHDGF) and another human HDGF gene (dbj|D 16431|HUMHDGF). These abovementioned genes are regarded as a family. So the functions of the HDGF2 can be deduced from the known functions of these genes and proteins.

Hepatoma-derived Growth Factor (HDGF) is a hepatin-binding protein isolated from human hepatoma-derived cell line HuH-7. HDGF has the activity of stimulating cell growth and promoting the growth of fibroblast and some heptoma cells (J. Biol. Chem. 269(40): 25143–25149, 1994). Though HDGF was firstly identified in hepatoma cells, Northern blotting analysis showed that it was expressed in human heart, brain, lung, liver, etc., and several tumor-derived cell lines (J. Biol. Chem. 269(40): 25143–25149, 1994). It needed further investigation to determine whether HDGF was expressed differently in normal cells and tumor cells (J. Biol. Chem. 269(40): 25143–25149, 1994). The functions of HDGF in hepatoma cells and its influence on hepatoma treatment would be revealed constantly as the researches were carried out. The expression patterns of the HDGF gene family members were different. However, they were all enriched in testis and the 5'-untranslated region contained GC-rich nucleotide sequences (GC content>70%) (Biochem. Biophys. Res. Comun. 238: 26–32, 1997). This property was similar to genes specifically expressed in testis or embryonic development, suggesting the potential important roles in male germ-cell development. They might also relate to DNA methylation, chromatin conformation, and translational regulation (J. Cell. Biol. 115: 887–903, 1990; Cell 62: 503–514, 1990).

It was revealed by immunofluoresence test that HDGF protein was located mainly in cytoplasm (J. Biol. Chem. 269(40): 25143–25149, 1994). The amino acid sequences of family members all contained a putative Nuclear Localization Signal (NLS), and none had any signal peptide sequence, which suggested they may play a role as a nucleoprotein. Fibroblast Growth Factor (FGF) was located in nuclear by this signal sequence to exert its mitogenic activity. Furthermore, the acidic amino acid sequence in the C-terminus of HDGF shared a high homology to that of HMG-1/-2 of HMG family and said sequence was known to be a histone-binding region in HMG-1/-2. (Biochemistry 29: 4419–4423, 1990). Summing up, it was likely that HDGF functions as a transcriptional factor to stimulate cell growth after internalization (Biochem. Biophys. Res. Comun. 238: 26–32, 1997). HDGF2 of the invention had similar activity.

The mitogenic activity of HDGF implied the great application value of HDGF in treating pernicious oxyhepatitis and liver injury (Clin. Chim. Acta. 183L 273–284, 1989). Researches indicated that many fibroblast growth factors were capable of promoting the growth of epithelial cells and could be widely applied to the vascularization defects, i.e., ischemia and atherosclerosis, and to neuron development (Blood 91(10): 3527–3561, 1998; Ann. N.Y. Acad. Sci. 545: 240–252, 1998). The application of HDGF1 and HDGF2 of the invention in promoting the growth of fibroblast needs further study.

The HDGF2 of the invention can be used not only as a member of the family in the study of function, but also to produce fusion proteins with other proteins, such as immunoglobulins. Besides, HDGF2 can be fused with or exchange fragments with other members of the family to form new proteins. For example, the N terminal of HDGF2 can exchange with the N terminal of HDGF1 or mice HDGF to produce proteins which are more active or have new properties.

The antibodies against HDGF2 can be used to screen other members of the family or to purify the related proteins such as other members of the family through affinity purification.

EXAMPLE 3

Expression of HDGF2 in *E. coli*

In this example, the cDNA sequence encoding HDGF2 was amplified with oligonucleotide PCR primers corresponding to 5'- and 3'-end of said DNA sequence. The resultant HDGF2 cDNA was used as an insertion fragment.

The sequence of 5'-end oligonucleotide primer was:

5'-CCACGGATCCATGGCGCGTCCGCGGCCCC-3' (SEQ ID NO: 5).

This primer contained a cleavage site of restriction endonuclease BamH I, followed by 19 nucleotides of HDGF2 coding sequence starting from the start codon.

The sequence of 3'-end primer was:

5'-ATCCGTCGACTTAGGTCCCTTCACTGGTT-3' (SEQ ID NO: 6).

This primer contained a cleavage site of restriction endonuclease SalI, a translation terminator and partial HDGF2 coding sequence.

These cleavage sites of restriction endonuclease in primers corresponded to the cleavage sites in bacterial expression vector pQE-9 (Qiagen Inc., Chatsworth, Calif.). Vector pQE-9 encodes an antibiotic resistance (Amp), a bacterial replication origin (ori), an IPTG-adjustable promotor/operon (P/O), a ribosome-binding site (RBS), a six-hisitine tag (6-His) and cloning sites of restriction endonuclease.

Vector pQE-9 and insertion fragments were digested by BamHI and SalI, and then linked together, ensuring that the open reading frame started from the bacterial RBS. Then, the linkage mixture was used to transform *E. coli* M15/rep4 (Qiagen) containing multi-copy of plasmid pREP4 which expressed-repressor of lacI and was resistant to kanamycin (Kan$^r$). Transformants were screened out in LB medium containing Amp and Kan. The plasmids were extracted. The size and direction of the inserted fragments were verified by PstI digestion. The sequencing confirmed that HDGF2 cDNA fragment was correctly inserted into the vector.

The positive clones of transformant were cultured overnight in LB liquid medium supplemented with Amp (100 ug/ml) and Kan (25 ug/ml). The overnight culture was 1:100–1:250 diluted, inoculated into large volume medium, and cultured until the 600 nm optical density ($OD_{600}$%) reached 0.4–0.6. IPTG (isopropylthio-beta-D-galactoside) was added to final concentration of 1 mM. By deactivating repressor of LacI, IPTG induced and promoted P/0, thereby increasing the expression of gene. The cells were cultured for another 3–4 hours, and then centrifuged (6000×g, 20 mins). The cultures were sonicated, and cell lysate was collected and diluted with 6M guanidine hydrochloride. After clarification, the dissolved HDGF2 in solution were purified by nickel-chelated column chromatography under the conditions suitable for the tight binding of 6-His tagged protein and column. HDGF2 was eluted with 6M guanidine hydrochloride (pH 5.0). The denaturalized proteins in guanidine hydrochloride were precipitated by several methods. First, guanidine hydrochloride was separated by dialysis. Alternatively, the purified protein, which was isolated from nickel-chelated column, bound to the second column with decreased linear gradient of guanidine hydrochloride. The proteins were denatured when binding to the column. Then, the proteins were eluted with guanidine hydrochloride (pH 5.0). Finally, the soluble proteins were dialyzed with PBS, then preserved in glycerol stock solution with the final glycerol concentration of 10% (w/v).

The molecular weight of the expressed protein was about 23 kDa, as identified by 12% SDS-PAGE.

Moreover, the sequencing results of the 10 amino acids at the N- and C-terminal of the expressed protein indicated that they were identical to those in SEQ ID NO: 4.

EXAMPLE 4

Expression of HDGF2 in Eukaryotic Cells (CHO Cell Line)

In this example, the cDNA sequence encoding HDGF2 was amplified with oligonucleotide PCR primers corresponding to 5'- and 3'-end of said DNA sequence. The resultant product was used as an insertion fragment.

The sequence of 5'-end oligonucleotide primer was:

5'-CCCTAAGCTTATGGCGCGTCCGCGGCCCC-3' (SEQ ID. NO: 7),

This primer contained a cleavage site of restriction endonuclease HindIII, followed by 19 nucleotides of HDGF2 coding sequence starting from the start codon.

The sequence of 3'-end primer was:

5'-TTTCGGATCCTTAGGTCCCTTCACTGGTT-3' (SEQ ID NO: 8)

This primer contained a cleavage site of restriction endonuclease BamHI, a translation stop codon, and partial HDGF2 coding sequence.

These cleavage sites of restriction endonuclease in primers corresponded to the cleavage sites in expression vector pcDNA3 for CHO cell. This vector encoded two kinds of antibiotic resistance (Amp$^r$ and Neo$^r$), a phage replication origin (f1 ori), a virus replication origin (SV40 ori), a T7 promoter, a virus promoter (P-CMV), a Sp6 promoter, a polyadenylation signal of SV40 and the corresponding polyA sequence thereof, a polyadenylation signal of BGH and the corresponding poly A sequence thereof.

The vector pcDNA3 and insertion fragment were digested with HindIII and BamHI, and linked together. Subsequently, *E. coli* strand DH5 α was transformed with linkage mixture.

Transformants were screened out in LB medium containing Amp. The clones containing the needed constructs were cultured overnight in LB liquid medium supplemented with Amp (100 ug/ml). Plasmids were extracted. The size and direction of the inserted fragments were verified by PstI digestion. The sequencing indicated that HDGF2 cDNA fragment was correctly inserted into the vector.

Plasmids were transfected into CHO cells by lipofection with Lipofectin Kit (GIBco Life). After transfecting the cells for 48 hours and screening the cells with G418 for 2–3 weeks, the cells and cell supernatant were collected and the activity of the expressed protein was measured. G418 was removed and the transformants were subcultured continuously. The mixed clonal cells were limiting diluted and the subclones with higher protein activity were selected. The positive subclones were mass cultured by routine methods. 48 hours later, the cells and supernatant were collected. The cells were ultrasonicated. Using 50 mM Tris-HCl (pH7.6) solution containing 0.05% Triton as an equilibrium solution and eluent, the active peek of the protein was collected with a pre-balanced Superdex G-75 column. Then, using 50 mM Tris-HCl (pH8.0) solution containing 0–1 M NaCl as an eluent, the protein was gradiently washed on a DEAE-Sepharose column balanced with 50 mM Tris-HCl (pH8.0) solution. The active peek of the protein was collected. The solution of the expressed protein was dialyzed with PBS (pH7.4), and finally lyophilized and preserved.

The molecular weight of the expressed protein was about 23 kDa as identified by 12% SDS-PAGE.

Moreover, the sequencing results of the 10 amino acids at the N- and C-terminal of the expressed protein indicated that they were identical to those in SEQ ID NO: 4.

EXAMPLE 5

Antibody Preparation

Antibodies were produced by immunizing animals with the recombinant proteins obtained in Examples 3 and 4. The method was as follows: the recombinant proteins were isolated by chromatography, and stored for use. Alternatively, the protein was isolated by SDS-PAGE electrophoresis, and obtained by cutting eletrophoretic bands from gel. The protein was emulsified with Freund's complete adjuvant of the same volume. The emulsified protein was injected intraperitoneally into mice at a dosage of 50–100 ug/0.2 ml. 14 days later, the same antigen was emulsified with Freund's incomplete adjuvant and injected intraperitoneally into mice at a dosage of 50–100 ug/0.2 ml for booster immunization. Booster immunization was carried out every 14 days, for at least three times. The specific activity of the obtained antiserum was evaluated by its ability of precipitating the translation product of HDGF2 gene in vitro.

All the documents cited herein are incorporated into the invention as reference, as if each of them is individually incorporated. Further, it is appreciated that, in the above teaching of the invention, the skilled in the art can make certain changes or modifications to the invention, and these equivalents are still within the scope of the invention defined by the appended claims of the present application.

What is claimed is:

1. An isolated DNA molecule comprising a nucleotide sequence encoding a polypeptide comprising an amino acid sequence of SEQ ID NO: 4.

2. The DNA molecule of claim 1 wherein said nucleotide sequence encodes a polypeptide consisting of an amino acid sequence of SEQ ID NO: 4.

3. The DNA molecule of claim 1 wherein said nucleotide sequence comprises the nucleotide sequence of nucleotides 121–732 in SEQ ID NO: 3.

4. A vector containing the DNA sequence of claim 1.

5. An isolated host cell transformed by the vector of claim 4.

6. The host cell of claim 5 which is *E. coli*.

7. The host cell of claim 5 which is an eukaryotic cell.

8. A method for producing human Hepatoma-derived growth factor-2 (HDGF2) protein, which comprises the steps of:

(a) forming an expression vector comprising the nucleotide sequence encoding HDGF2 protein comprising the amino acid sequence of SEQ ID NO: 4, wherein said nucleotide sequence is operably linked with a vector expression regulatory sequences;

(b) introducing the vector of step (a) into a host cell, thereby forming a recombinant host cell for producing HDGF2 protein;

(c) culturing the recombinant cell of step (b) under the conditions suitable for expression of HDGF2 protein; and (d) isolating the HDGF2 protein.

9. The method of claim 8 wherein said nucleotide sequence comprises nucleotides 121–732 of SEQ ID NO: 3.

* * * * *